US011584952B2

(12) United States Patent
Pack et al.

(10) Patent No.: US 11,584,952 B2
(45) Date of Patent: Feb. 21, 2023

(54) METHOD FOR PREPARING DNA OLIGOMER INTO WHICH SINGLE NUCLEOTIDE IS INCORPORATED USING TERMINAL DEOXYNUCELOTIDYL TRANSFERASE

(71) Applicant: Korea University Research and Business Foundation, Sejong Campus, Sejong (KR)

(72) Inventors: Seung Pil Pack, Sejong (KR); Eui Kyoung Jang, Sejong (KR)

(73) Assignee: KOREA UNIVERSITY RESEARCH AND BUSINESS FOUNDATION, SEJONG CAMPUS, Sejong (KR)

( * ) Notice: Subject to any disclaimer, the term of this patent is extended or adjusted under 35 U.S.C. 154(b) by 148 days.

(21) Appl. No.: 16/758,523

(22) PCT Filed: Oct. 12, 2018

(86) PCT No.: PCT/KR2018/012038
§ 371 (c)(1),
(2) Date: Apr. 23, 2020

(87) PCT Pub. No.: WO2019/083204
PCT Pub. Date: May 2, 2019

(65) Prior Publication Data
US 2020/0340037 A1   Oct. 29, 2020

(30) Foreign Application Priority Data
Oct. 27, 2017   (KR) ........................ 10-2017-0140908
Oct. 12, 2018   (KR) ........................ 10-2018-0121604

(51) Int. Cl.
*C12Q 1/6806*   (2018.01)
(52) U.S. Cl.
CPC .................................. *C12Q 1/6806* (2013.01)
(58) Field of Classification Search
CPC ................................................... C12Q 1/6806
See application file for complete search history.

(56) References Cited

U.S. PATENT DOCUMENTS

| | | | | |
|---|---|---|---|---|
| 4,851,331 A | * | 7/1989 | Vary .................... | C12Q 1/6813 435/6.12 |
| 6,406,890 B1 | * | 6/2002 | Mueller ............... | C12N 9/1264 435/252.3 |
| 2008/0160581 A1 | | 7/2008 | Getts et al. | |
| 2011/0306099 A1 | * | 12/2011 | Beasley ................. | C12N 15/66 435/91.41 |
| 2017/0037465 A1 | * | 2/2017 | Tsavachidou ........ | C12Q 1/6806 |

OTHER PUBLICATIONS

Jang et al. (Post Art) Novel enzymatic single-nucleotide modification of DNA oligomer: prevention of incessant incorporation of nucleotidyl transferase by ribonucleotide-borate complex, 2019, Nucleic Acids Research, 47, No. 17, e102, pp. 1-11. (Year: 2019).*
International Search Report dated Jan. 29, 2019 in corresponding International Patent Application No. PCT/KR2018/012038 (3 pages in English, 3 pages in Korean).
Fowler et al., "Biochemical, Structural, and Physiological Characterization of Terminal Deoxynucieotidyl Transferase," Chemical Reviews, 2006, vol. 106, pp. 2092-2110.
Li et al., "Kinetics of RNA Degradation by Specific Base Catalysis of Transesterification Involving the 2¢-Hydroxyl Group," Journal of the American Chemical Society, 1999, vol. 121, pp. 5364-5372.
Furukawa et al., "Borate and the Origin of RNA: A Model for the Precursors to Life," Elements, Aug. 2017, vol. 13, pp. 261-265.
Boule et al., "Terminal Deoxynucieotidyl Transferase Indiscnmmately Incorporates Ribonudeotides and Deoxyribonucleotides," Journal of Biological Chemistry, Aug. 17, 2001, vol. 276. No. 33. pp. 31388-31393.
Jang et al., "Design of reactive-end DNA oligomers via incorporation of oxanine into oligonucleotides using terminal deoxynucieotidyl transferase," Process Biochemistry, (electronic publication) Jul. 28, 2017, vol. 62, pp. 99-105.
Pack et al., "Labelling of Single Ribonucleotide by TdT for Crosslinking," In: 2018 KSBB International Academia-industry Joint Meeting, Oct. 11, 2018. Poster Presentation P0926, Sejong University Convention Center, Seoul, Republic of Korea.
Jang et al., "Single Modified-nucleotide Incorporation Exposing an Active 3'-OH Terminus via Terminal Deoxynucieotidyl Transferase (Tdt) Assisted by Ribose-borate Complexation," In: 2017 KSBB Fall Meeting and International Symposium, Oct. 13, 2017, Oral Presentation of Student OP208, Bexco, Busan, Republic of Korea.
Jang et al., "Novel Enzymatic Single-Nucleotide Labeling of a DNA Oligomer with a Modified Nucleotide using an Inhibitory Effect of a Ribose-Borate Complex on TdT," In: 2018 KSBB Spring Meeting and International Symposium, Apr. 19, 2018, Poster Presentation p. 1014. Yeosu The Ocean Resort, Yeosu, Republic of Korea.
Jang et al., "Stalled Chain Elongation in Enzymatic Post DNA Modification Driven by Ribose-borate Substrate," In: KMB 20 I8 45th Annual Meeting & International Symposium, Jun. 28, 2018, Poster Presentation, Yeosu Expo Convention Center, Yeosu, Republic of Korea.

* cited by examiner

*Primary Examiner* — Narayan K Bhat
(74) *Attorney, Agent, or Firm* — NSIP Law

(57) ABSTRACT

The present invention relates to a method for preparing a DNA oligomer into which a single nucleotide is incorporated using a terminal deoxynucleotidyl transferase. According to the present invention, by using a base hydrolysis reaction or a ribose-borate complex formation method, single incorporation of normal and modified nucleotides in a TdT enzyme-based DNA oligomer modification method can be facilitated. In addition, the method simultaneously provides the usability of TdT and the quantitativeness of modification group incorporation, thereby being effectively usable in the development of a quantitative detection technique or in a crosslinking reaction, both of which require quantitativeness and, according to the present invention, a DNA oligomer, into which a single nucleotide which is a product of a TdT reaction is incorporated, has an exposed a 3' hydroxyl terminus, which is an enzyme recognition site, such that an additional enzymatic technique such as primer extension or ligation can be introduced.

2 Claims, 6 Drawing Sheets
Specification includes a Sequence Listing.

METHOD FOR PREPARING DNA OLIGOMER INTO WHICH SINGLE NUCLEOTIDE IS INCORPORATED USING TERMINAL DEOXYNUCELOTIDYL TRANSFERASE

CROSS REFERENCE TO RELATED APPLICATIONS

This application is a U.S. National Stage Application of International Application No. PCT/KR2018/012038, filed on Oct. 12, 2018, which claims the benefit under 35 USC 119(a) and 365(b) of Korean Patent Application Nos. 10-2017-0140908 filed on Oct. 27, 2017, and 10-2018-0121604 filed on Oct. 12, 2018, in the Korean Intellectual Property Office, the entire disclosures of which are incorporated herein by reference for all purposes.

TECHNICAL FIELD

The present invention relates to methods for preparing single-nucleotide incorporated DNA oligomers using terminal deoxynucleotidyl transferase.

INCORPORATION-BY-REFERENCE OF MATERIAL SUBMITTED BY U.S.P.T.O. EFS-WEB

The instant application contains a Sequence Listing, which is being submitted in computer readable form via the United States Patent and Trademark Office eFS-WEB system and which is hereby incorporated by reference in its entirety for all purposes. The txt file submitted herewith contains a 1.15 KB file (OA20211217_J10159.0006_SequenceListing.txt).

INCORPORATION-BY-REFERENCE OF MATERIAL SUBMITTED BY U.S.P.T.O. EFS-WEB

The instant application contains a Sequence Listing, which is being submitted in computer readable form via the United States Patent and Trademark Office eFS-WEB system and which is hereby incorporated by reference in its entirety for all purposes. The txt file submitted herewith contains a 1811 bytes file, which was created on Sep. 26, 2022 (EX20220922 J101590006 AmendedSeqListing.txt).

BACKGROUND ART

DNA oligomers are biomaterials that possess self-assembly properties and are utilized as essential materials for nanobiotechnology research aimed at the development of DNA-based sensors, drug delivery systems or new catalysts. The self-assembly of DNA is determined by combinations of the four nucleobases (adenine-thymine and guanine-cytosie) present in normal nucleotides (NTs) and acts as a basic factor in the construction of 2- and 3-dimensional structures and the design of temperature-based on/off switches. On the other hand, DNA molecules composed of combinations of normal NTs are limited in their function. According to many DNA application examples reported to date, DNA constructs work with probing or functional accessory molecules (for example, coenzymes, peptides, proteins, and lipids). Such functional diversification is enabled by the modification of DNA oligomers in which conjugates with accessory molecules or modified nucleotides capable of binding to the conjugates are incorporated into DNA.

Methods for modifying DNA oligomers using enzymes are based on post-modification and have an advantage in that customized substrates can be introduced depending on research purposes. Due to this advantage, enzymatic modification of DNA oligomers is used as a promising tool for research and development. In recent years, a large number of modified NTs have been developed for DNA modification enzymes such as DNA polymerases and ligases and most of them are in the form of nucleotide triphosphates (NTPs) as enzyme substrates. Terminal deoxynucleotidyl transferase (TdT) is a kind of DNA polymerase that is widely used as a DNA modification enzyme due to its ability to incorporate non-specific substrates into the ends of single-stranded DNA molecules. TdT is easy to use due to its ability to incorporate NTs without the help of a template strand but is incapable of controlling the extension length of incorporated NTs, limiting its use. For example, TdT is useful in incorporating several signal substrates for the purpose of signal amplification in apoptosis measurement or gene probing, but single reactive groups cannot be incorporated for quantitative crosslinking without the use of special substrates for the prevention of incessant extension. Here, the special substrates are dideoxynucleotide triphosphates (ddNTPs) developed for the purpose of DNA sequencing. However, the number of reactive groups developed hitherto is incomparable to that of normal and modified NTs and their use is limited because an additional process such as primer extension or ligation cannot be introduced.

DETAILED DESCRIPTION OF THE INVENTION

Problems to be Solved by the Invention

The present invention has been made in an effort to solve the above-described problems and intends to provide methods for preparing DNA oligomers modified with single incorporation of normal and modified nucleotide in order to maximize the utilization of TdT-based DNA modification.

Means for Solving the Problems

One aspect of the present invention provides a method for preparing a single-nucleotide (NT) incorporated DNA oligomer, including (a) preparing a DNA oligomer and a plurality of ribonucleotide triphosphates (rNTPs), (b) allowing the DNA oligomer to react with the plurality of rNTPs in the presence of a TdT reaction buffer containing Tris-acetate such that the plurality of rNTPs continuously bind to and extend from the 3'-end of the DNA oligomer, and (c) adding an alkaline solution to the extension product to induce alkaline hydrolysis such that the bonds between the extended rNTPs are cleaved to leave the single-incorporated rNTP at the 3'-end of the DNA oligomer.

Another aspect of the present invention provides a method for preparing a single-nucleotide (NT) incorporated DNA oligomer, including (a) preparing a DNA oligomer and a plurality of ribonucleotide triphosphates (rNTPs) and (b) allowing the DNA oligomer to react with the plurality of rNTPs in the presence of a TdT reaction buffer containing Tris-borate such that a ribose-borate complex is formed to inhibit the bonding between the plurality of rNTPs, leaving the single-incorporated rNTP at the 3'-end of the DNA oligomer.

According to the present invention, the rNTP may be selected from the group consisting of adenosine triphosphate (ATP), uridine triphosphate (UTP), guanosine triphosphate (GTP), oxanosine triphosphate (OTP), $N^6$-propargyl-ATP (N6P-ATP), aminoallyl-UTP (AA-UTP), biotin-16-UTP (Bt-UTP), and combinations thereof.

According to the present invention, the alkaline solution may be selected from the group consisting of LiOH, NaOH, KOH, CsOH, RbOH, $Mg(OH)_2$, $Ca(OH)_2$, $Sr(OH)_2$, $NH_4OH$, $Ba(OH)_2$ solutions, and mixtures thereof.

Effects of the Invention

The methods of the present invention facilitate single incorporation of normal and modified nucleotide into DNA oligomers using TdT based on alkaline hydrolysis or ribose-borate complex formation. In addition, the easy-to-use TdT and the quantitative incorporation of a modified group are useful for crosslinking reactions needing to be quantified and the development of quantitative detection techniques. Furthermore, DNA oligomers prepared by the methods of the present invention have an exposed 3'-hydroxyl group that can be recognized by an enzyme, advantageously enabling the introduction of an additional enzymatic process such as primer extension or ligation.

BRIEF DESCRIPTION OF THE DRAWINGS

FIG. 8 shows the results of single-NT incorporation based on ribose-borate complex formation according to the method of the present invention. For the single incorporation, four modified NTs were used. (A) Oxanine, (B) biotin, (C) aminoallyl, and (D) $N_6$-propargyl groups as reactive groups were incorporated into DNA and reacted with poly-L-lysine, streptavidin, N-hydroxysuccinimide (NHS)-labeled Cy5 dye, and azide-labeled Cy5, respectively, to investigate their reactivities. (E) shows the total concentrations of NTs incorporated by enzymatic reactions and the proportions of the single incorporated NTs, which were quantitatively measured by PAGE analysis. The single-NT incorporation efficiencies amounted to ≥80%, which correspond to ligation efficiencies of 64.5-77.5%. Since the ribose-borate complex formation is a reversible reaction, the 3'-OH group is exposed after sequence purification and can be recognized as a substrate by a ligase. Gel analysis revealed that no ligation occurred in extension products of two or more nucleotides.

BEST MODE FOR CARRYING OUT THE INVENTION

The present invention will now be described in more detail.

The present invention intends to provide methods for preparing DNA oligomers modified with single incorporation of normal and modified nucleotide in order to maximize the utilization of TdT-based DNA modification.

Thus, the present invention provides a method for preparing a single-nucleotide (NT) incorporated DNA oligomer, including (a) preparing a DNA oligomer and a plurality of ribonucleotide triphosphates (rNTPs), (b) allowing the DNA oligomer to react with the plurality of rNTPs in the presence of a TdT reaction buffer containing Tris-acetate such that the plurality of rNTPs continuously bind to and extend from the 3'-end of the DNA oligomer, and (c) adding an alkaline solution to the extension product to induce alkaline hydrolysis such that the bonds between the extended rNTPs are cleaved to leave the single-incorporated rNTP at the 3'-end of the DNA oligomer.

The present invention also provides a method for preparing a single-nucleotide (NT) incorporated DNA oligomer, including (a) preparing a DNA oligomer and a plurality of ribonucleotide triphosphates (rNTPs) and (b) allowing the DNA oligomer to react with the plurality of rNTPs in the presence of a TdT reaction buffer containing Tris-borate such that a ribose-borate complex is formed to inhibit the bonding between the plurality of rNTPs, leaving the single-incorporated rNTP at the 3'-end of the DNA oligomer.

The rNTP is preferably selected from the group consisting of, but not necessarily limited to, adenosine triphosphate (ATP), uridine triphosphate (UTP), guanosine triphosphate (GTP), oxanosine triphosphate (OTP), $N^6$-propargyl-ATP (N6P-ATP), aminoallyl-UTP (AA-UTP), biotin-16-UTP (Bt-UTP), and combinations thereof.

The alkaline solution is preferably selected from the group consisting of, but not necessarily limited to, LiOH, NaOH, KOH, CsOH, RbOH, $Mg(OH)_2$, $Ca(OH)_2$, $Sr(OH)_2$, $NH_4OH$, $Ba(OH)_2$ solutions, and mixtures thereof.

MODE FOR CARRYING OUT THE INVENTION

The present invention will be explained in more detail with reference to the following examples. It will be appreciated by those skilled in the art that these examples are merely illustrative and are not intended to limit the scope of the present invention.

Methods

Preparation of DNA Oligomers and Reagents

Oligodeoxynucleotides (ODNs) were prepared by a commercial service (Integrated DNA Technologies Co., Coralville, Iowa, USA) as follows: DNA oligomer for optimization of oxanine incorporation F-10dA, FAM is attached to 5' end of the nucleotide sequence having SEQ ID NO: 1), an upstream fragment for ligation testing F-20dN FAM is attached to 5' end of the nucleotide sequence having SEQ ID NO: 2), a downstream fragment (SEQ ID NO: 3), and a template fragment (SEQ ID NO:4, SEQ ID NO:5, SEQ ID NO:6, or SEQ ID NO:7). TdT and ligase were purchased from New England BioLabs (NEB, Ipswich, Mass.). Normal and modified NTs except OTP were purchased from reagent companies: AA-UTP (Thermo); Biotin-16-UTP (ROCHE); GTP, ATP, UTP, N6P-ATP (Sigma Aldrich). OTP was chemically synthesized from GTP.

OTP Synthesis

OTP was synthesized by the following procedure. 10 mg of dGTP was dissolved in 2.6 mL of DW and 1 mL of 4 M acetate buffer (pH 3.7) was added thereto. The mixture was preheated at 40° C. for 5 mM, and then 0.4 mL of 1 M $NaNO_2$ (final 100 mM) was further added thereto. After incubation at 40° C. for 4 h, the mixture was neutralized by adding NaOH to stop the reaction. OTP was purified by HPLC purification (Young Lin Co., Korea, YL9100 system, Column: ULTRON VX-ODS 150×6.0 mm, 5 μm; gradient buffer system: 0% ACN in 100 mM TEAA at 0 min to 20% ACN in 100 mM TEAA at 20 min, 1 mL/min flow rate) and lyophilized.

Single-NT Incorporation Based on Alkaline Hydrolysis

A single NT was incorporated based on alkaline hydrolysis by a method including (a) preparing a DNA oligomer and a plurality of ribonucleotide triphosphates (rNTPs), (b) allowing the DNA oligomer to react with the plurality of rNTPs in the presence of a TdT reaction buffer containing Tris-acetate such that the plurality of rNTPs continuously bind to and extend from the 3'-end of the DNA oligomer, and (c) adding an alkaline solution to the extension product to induce alkaline hydrolysis such that the bonds between the extended rNTPs are cleaved to leave the single-incorporated rNTP at the 3'-end of the DNA oligomer.

First, 25 μL of a mixture of a DNA oligomer (final 4 μM), rNTPs (final 80-200 μM), $CoCl_2$ [final 0.25 mM (1×), NEB], 10× TdT reaction buffer (Tris Acetate) (final 1×, NEB), and TdT (10 units) was incubated at 37° C. for 90 mM. As a result, the plurality of rNTPs were allowed to continuously bind to and extend from at the 3'-end of the DNA oligomer.

Next, 20 μL of 0.1 M NaOH was added, followed by incubation at 90° C. for additional 60 mM to yield a DNA oligomer in which a single ribonucleotide was incorporated at the terminal phosphate group (ODNs-1rNp).

Single-NT Incorporation Based on Ribose-Borate Complex Formation

A single NT was incorporated based on ribose-borate complex formation by a method including (a) preparing a DNA oligomer and a plurality of ribonucleotide triphosphates (rNTPs) and (b) allowing the DNA oligomer to react with the plurality of rNTPs in the presence of a TdT reaction buffer containing Tris-borate such that a ribose-borate complex is formed to inhibit the bonding between the plurality of rNTPs, leaving the single-incorporated rNTP at the 3'-end of the DNA oligomer.

First, a DNA oligomer (final 3 μM) was mixed with modified rNTPs (150 μM rOTP, 200 μM N6P-ATP, 50 μM AA-UTP, 200 μM Bt-UTP) in a borate-containing buffer (100 mM Tris, 100 mM borate, 0.25 mM $CoCl_2$, 10 mM $MgCl_2$, pH 8.0 at 25° C.) together with TdT (10 units, NEB). The mixture (final 25 μL) was incubated at 37° C. for 60 mM. To stop the reaction, 4 μL of 0.3 M EDTA was added to the reaction mixture to deactivate the TdT. The resulting mixture was heated at 90° C. for 10 mM. Residual rNTPs and buffer components were removed by means of a 3 kDa MWCO (molecular weight cut-off) filter (Amicon TM, Merck KGaA, Darmstadt, Germany) or a desalting column.

Ligation of the TdT Reaction Product Obtained Based on Ribose-Borate Complex Formation The TdT reaction product obtained based on ribose-borate complex formation was purified by means of a centrifugal filter (3 kDa MWCO), where buffer components and residual rNTPs were removed. The purified product as the upstream ligation fragment was mixed with the downstream ligation fragment and the template fragment in a ratio of 1:1.2:1.2 μM in a ligation buffer. The ligase was added to the mixture, followed by incubation at 37° C. for 2 h. The ligation product was analyzed by denaturing PAGE in 12% 7 M urea.

PAGE Analysis and Quantification

Reaction products in which rNTP-incorporated DNA and unreacted DNA coexisted were separated and analyzed by denaturing PAGE in 7 M urea (16% gel). A signal from the FAM dye (ex 495 nm/em 520 nm) labeled at the 5'-end of each DNA sequence was detected and quantified using a fluorescence image analyzer (LAS 4000, General Electric Co.).

Results and Discussion

Figure 1:
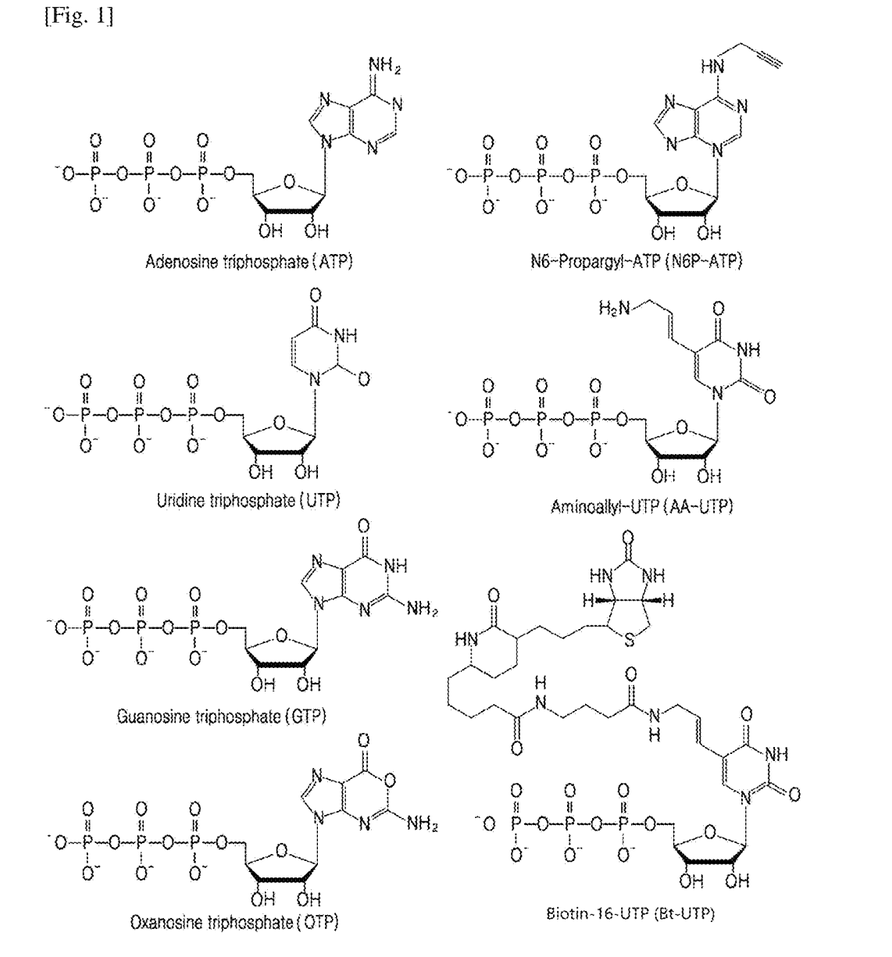
FIG. 1 shows the structures of normal and modified ribonucleotide triphosphates (rNTPs) as substrates for TdT reactions.
Figure 2:
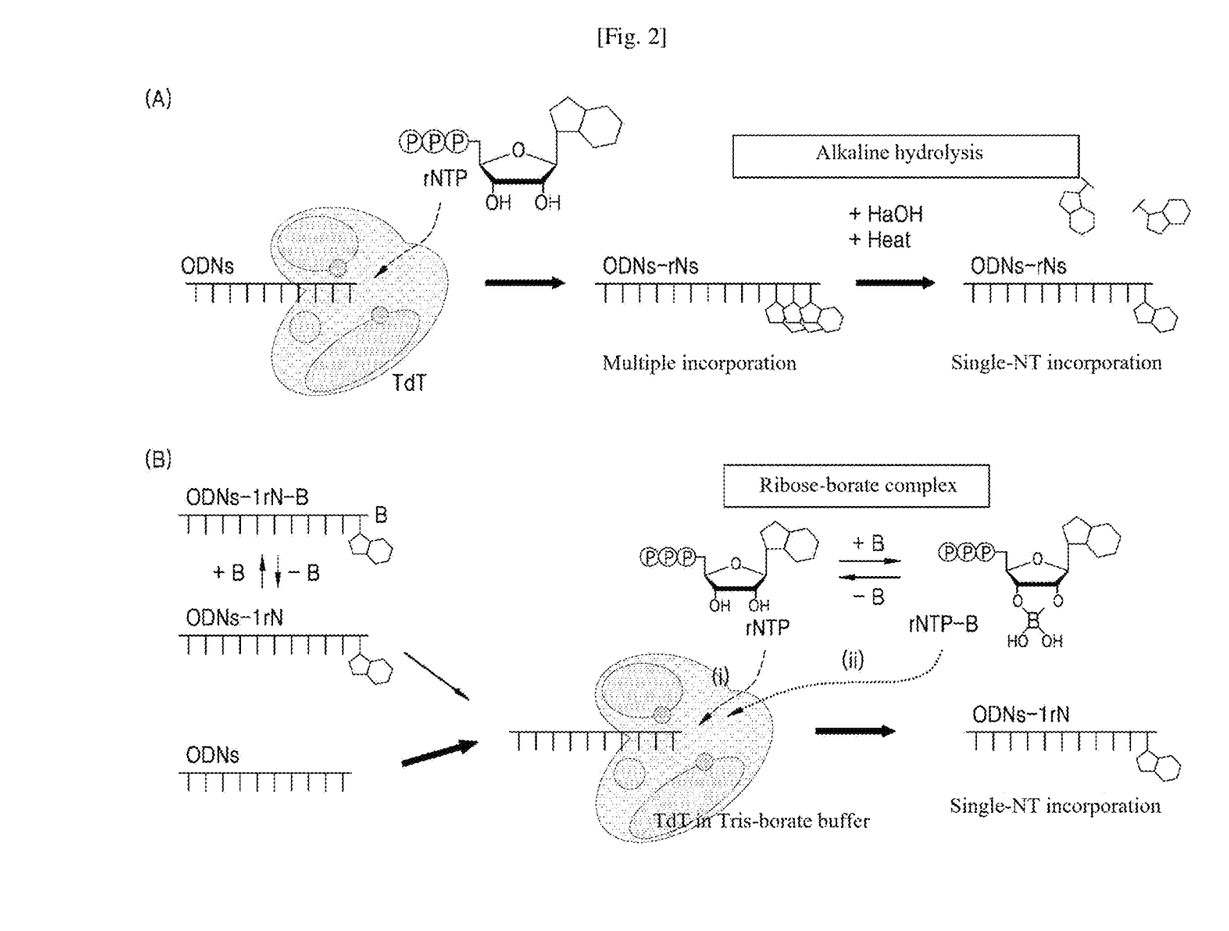
FIG. 2 shows the principles of methods for preparing single-nucleotide incorporated DNA oligomers using TdT reactions according to the present invention: (A) the principle of a method for preparing a single-nucleotide incorporated DNA oligomer based on alkaline hydrolysis; and (B) the principle of a method for preparing a single-nucleotide incorporated DNA oligomer based on ribose-borate complex formation.
Figure 3:
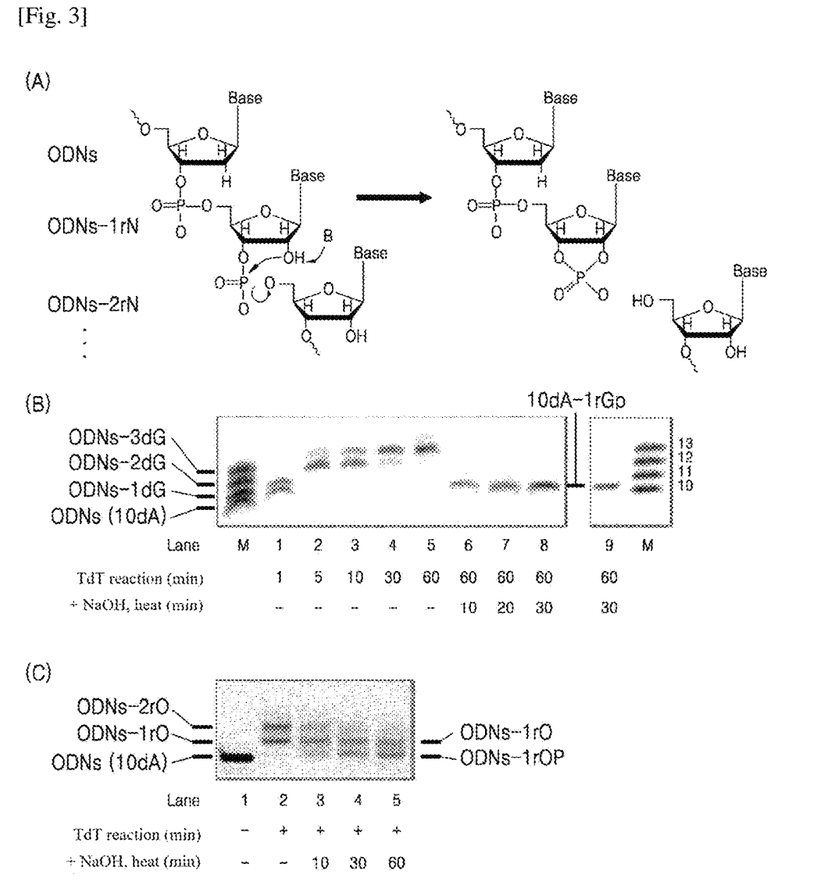
FIG. 3 shows single-ribonucleotide incorporation using rNTPs as substrates and alkaline hydrolysis: (A) the principle in which rNTPs are self-hydrolyzed when the 2'-OH group of ribose attacks the 3'-phosphate linkage in alkaline conditions, leaving a single ribonucleotide at the end of a DNA oligomer; (B) the results of single guanine incorporation using rGTP substrates; and (C) the results of single oxanine incorporation using rOTP substrates. The images showing the reaction results were taken through FAM dye labeled at the 5'-end of the DNA sequence (ODNs) after separation by 16% denaturing PAGE.

Single-NT incorporation based on alkaline hydrolysis A single ribonucleotide was incorporated via two reactions: continuous extension of rNTPs as substrates of TdT (FIG. 1); and alkaline hydrolysis of the extension product ((A) of FIG. 2). The rNTPs can be hydrolyzed when the 2'-hydroxyl groups of the ribonucleotides attack the phosphate groups of the extension product in an alkaline environment due to their catalytic activity ((A) of FIG. 3). The two or more extended NTs at the 3'-end of the DNA oligomer by TdT were converted to the single ribonucleotide-incorporated sequence (10dA-1rNp) by hydrolysis under heating after addition of an alkaline solution (NaOH). Here, normal and modified NT models (rGTPs and rOTPs) were used as substrates of TdT and subjected to alkaline hydrolysis ((B) and (C) of FIG. 3). As a result, the continuously incorporated rGTPs were hydrolyzed under alkaline conditions for ≥10 min. The hydrolysis led to a reduction in the molecular weight of the extension product and an increased sequence length of the single-ribonucleotide incorporated DNA oligomer (lanes 6-9 in (B) of FIG. 3). For the rOTPs, the single extension product (ODNs-1rO) remained unhydrolyzed (lanes 3-5 in (C) of FIG. 3). The reason why the sequence of the hydrolysis product underlay the corresponding oligomer size is because the negative charge of the phosphate group remaining at the 3'-end moved a larger distance on gel by the application of an electric field during electrophoresis than when the phosphate group was absent.

Single-NT Incorporation Based on Ribose-Borate Complex Formation

Figure 4:
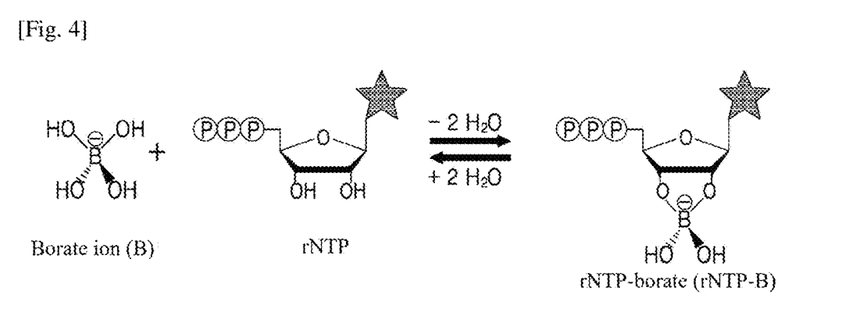
FIG. 4 shows the principle of single-ribonucleotide incorporation based on ribose-borate complex formation. The borate ion binds reversibly to the 2'- and 3'-OH groups in ribose to form a ribose-borate complex, which inhibits incessant rNTPs extension by TdT reactions to enable single-nucleotide incorporation.
Figure 5:
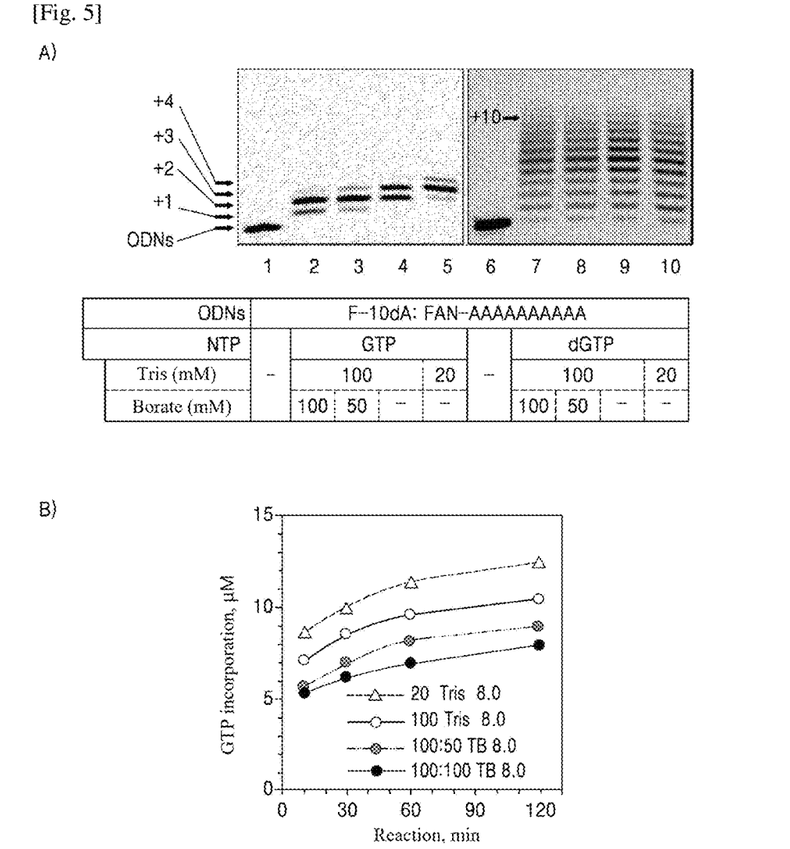
FIG. 5 shows the results of single-base incorporation using rGTPs as normal substrates and ribose-borate complex formation: (A) 16% denaturing PAGE (7 M urea) analysis revealed that rGTP-borate complex formation deteriorated the efficiency of rGTP incorporation. Since dGTP forms no complex, no inhibitory effect on rGTPs extension was found; and (B) time-course quantification of the concentrations of NTs incorporated in TdT reaction buffers containing different borate concentrations from the PAGE results, showing an increased inhibitory effect on rGTPs extension with increasing borate concentration in the reaction buffers.
Figure 6:
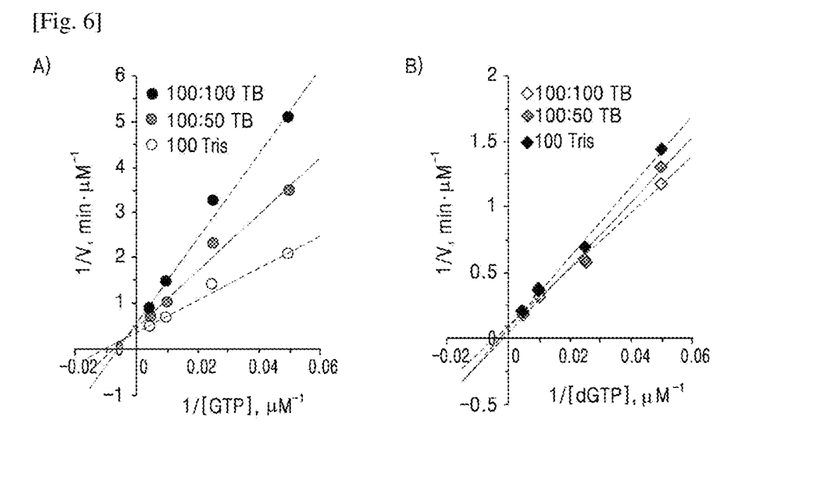
FIG. 6 shows the initial rates of TdT reactions. The presence of borate in reaction buffers was found to inhibit the activity of TdT on rGTPs (A), unlike on dGTPs (B). The initial rates of rGTP and dGTP incorporation were determined by PAGE analysis of reaction products between 0.5 and 2 mM, followed by quantification.

As shown in FIG. 4, boric acid and ribose are subjected esterification to form a complex. Based on this phenomenon, complexes of rNTPs as substrates of TdT with boric acid were formed to induce inhibition of the terminal deoxynucleotidyl transfer of TdT ((B) of FIG. 2). The enzyme and the reagents participated in the reaction were the same as those used for the alkaline hydrolysis, except that Trisacetate buffer was replaced by Tris-borate buffer. First, two types of guanine bases (rGTP, dGTP), which are substrates having the highest affinity for TdT, were used to compare the inhibitory effects of boric acid on rGTPs and dGTPs extensions. The ribose-borate complex is formed by bonding between the two 2'- and 3'-OH groups present in ribose and boric acid. In contrast, deoxyribose without 2'-OH group forms no ribose-borate complex with boric acid. Accordingly, it is anticipated that the addition of boric acid will have no inhibitory effect on dGTPs extension. The extension of rGTPs was found to be inhibited in proportion to the concentration of borate (lanes 2-4). In contrast, there was no inhibitory effect of boric acid addition on dGTPs extension (lanes 7-9). The same inhibitory effect on rGTPs extension was also observed in the results obtained after the enzymatic reaction for 2 h ((B) of FIG. 5). In addition, the presence of borate was found to inhibit the TdT reaction, which was demonstrated by measuring the enzymatic reaction rates (FIG. 6). Decreased accessibility to the substrates (increased $K_m$) and reduced enzymatic reaction rate (decreased $K_{cat}$) ("mixed inhibitory effect") were observed in accordance with the increased borate concentration in the reaction buffer. In contrast, when dGTPs were used as substrates ((B) of FIG. 6), no inhibition of TdT reaction was observed despite increasing borate concentration because borate ion cannot bind to the deoxyribose form dGTP. These results indicate that the addition of boric acid has no direct influence on the activity of TdT.

Figure 7:
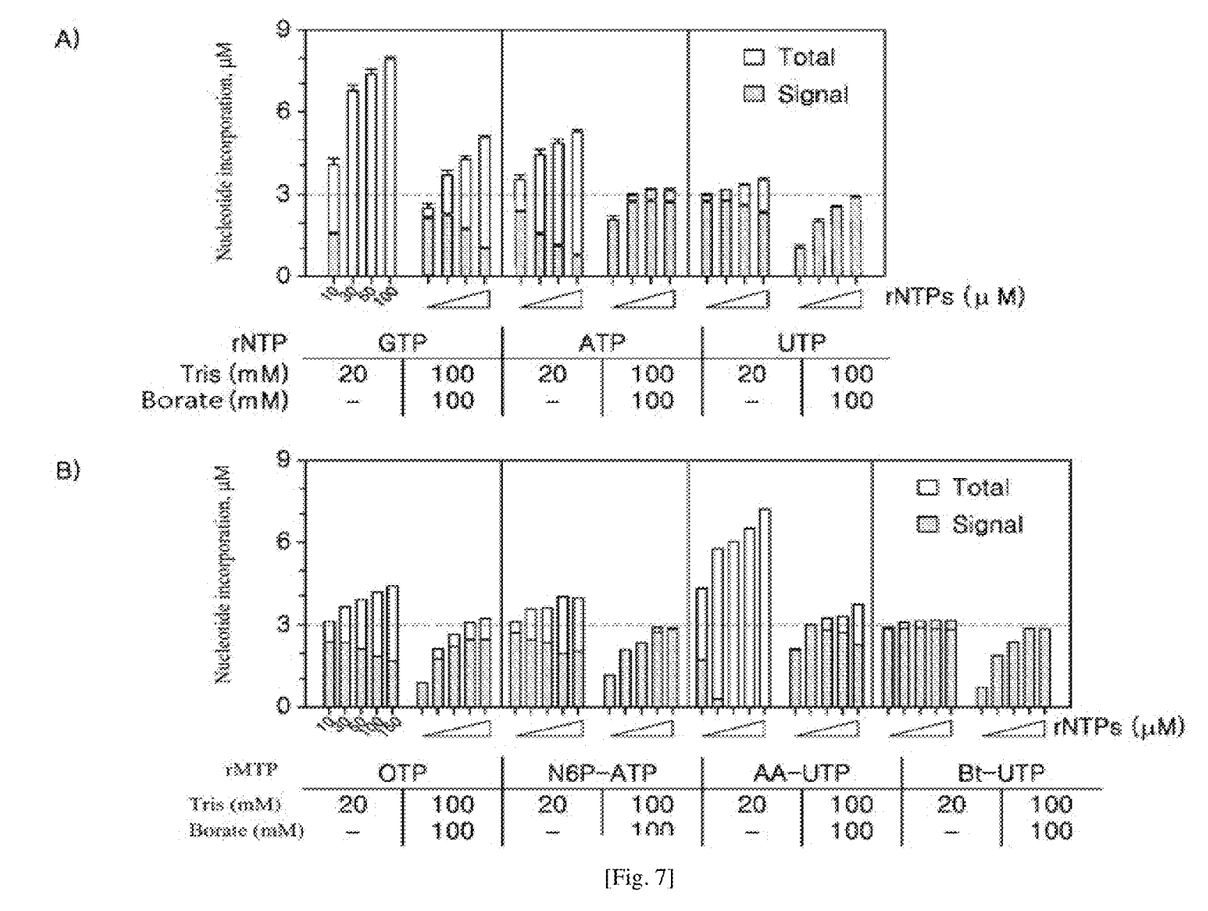
FIG. 7 shows the reaction efficiencies measured when a general reaction buffer (20 mM Tris-HCl, pH 8.0) and a borate-containing buffer (100 mM Tris-100 mM borate, pH 8.0) were used in a method for single-base incorporation based on ribose-borate complex formation according to the present invention. 3 µM DNA (F-10dA, 10 nt) was used. The yield and purity of the single-nucleotide incorporated product (11 nt) increased as its concentration approximated 3 µM. As a result, the use of the borate-containing reaction buffer was found to lead to a significant increase in reaction efficiency. The results were obtained by quantifying the PAGE results.

When other modified NTs (FIG. 1) were used, the yields and purities of the single-ribonucleotide incorporated products in borate-containing reaction buffers increased (FIG. 7), like when rGTPs were used. When TdT reactions were allowed to proceed in borate-containing buffers (100 mM Tris-100 mM borate, pH 8.0), the concentrations of the single-incorporated NTs in all rNTPs incorporation reactions approximated the initial concentration of the DNA oligomer (3 µM, indicated by dashed lines) and the total/single introduction ratios decreased. However, incessant elongation of nucleotides was observed overall in normal buffers (20 mM Tris-HCl, pH 8.0). Therefore, the use of the method based on ribose-borate complex formation enables a TdT reaction that is not susceptible to the type and concentration of NTs and can give a single-NT incorporated DNA oligomer with high purity in high yield.

Figure 8:
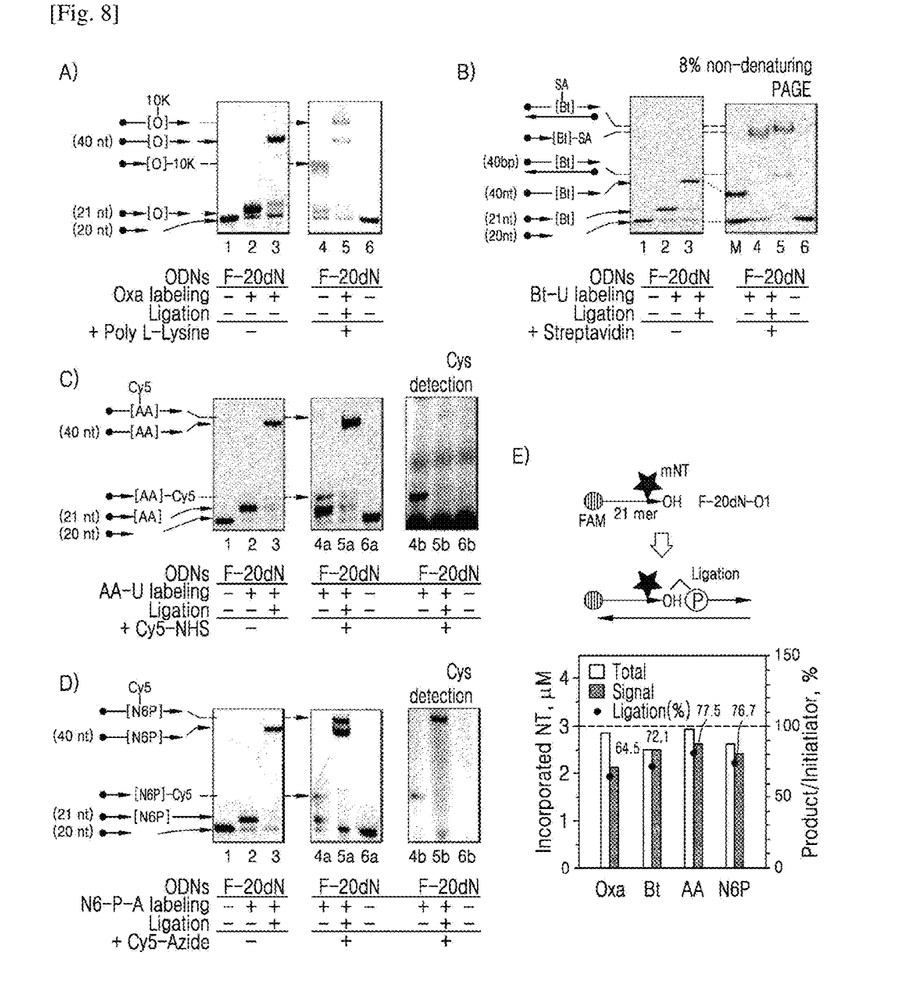

The ribose-borate complex formation is reversible and depends on the borate concentration. The 3'-borate binding to the terminal ribose of the single-NT incorporated product is removed by removal of the borate-containing buffer after purification. The 3'-OH group exposed after removal of the 3'-borate can be used for secondary enzymatic synthesis. Each modified NT was incorporated into the 20-mer DNA oligomer (F-20dN) in an optimized reaction. The NT incorporated DNA oligomer as a secondary reaction model was subjected to ligation. An extended sequence for ligation was designed to have a single nucleotide gap from F-20dN. Due to this design, no ligation occurs in extension products having two or more incorporated NTs. Since the ribose-borate complex formation is reversible, the 3'-OH group is exposed after sequence purification. The exposed OH group can be recognized as a substrate by a ligase. As a result of denaturing PAGE analysis, the single-NT incorporation efficiency amounted to ≥80%, which corresponds to a ligation efficiency of 64.5-77.5% ((E) of FIG. 8). Each of the ligation product with the single-NT incorporated DNA and the TdT product was reacted with a partner marker reacting with the corresponding modified NT ((A)-(D) of FIG. 8). The conjugate of the modified NT-containing DNA oligomer and the marker was located at an expected position on PAGE. From this observation, it could be concluded that the functionality of each NT was maintained after the TdT reaction and ligation (lanes 4a, 5a in A)-D) of FIG. 8).

According to the method of the present invention based on alkaline hydrolysis, a single-ribonucleotide incorporated DNA oligomer is prepared by allowing rNTPs to continuously bind to and extend from the 3'-end of a DNA oligomer and hydrolyzing the extension product. The alternative method of the present invention is based on ribose-borate complex formation to prevent incessant rNTPs extension by TdT reactions. The methods of the present invention facilitate single incorporation of ribonucleotide triphosphate (rNTP) as an enzyme substrate. Since the 3'-hydroxyl group recognized by a DNA modification enzyme is preserved in the final single-ribonucleotide incorporated DNA oligomer, the terminal hydroxyl group can be utilized for additional modification synthesis or the construction of a secondary product by a suitable process such as primer extension or ligation.

INDUSTRIAL APPLICABILITY

The methods of the present invention are useful for crosslinking reactions needing to be quantified or the development of quantitative detection techniques. Single-nucleotide incorporated DNA oligomers prepared by the methods of the present invention are TdT reaction products and have an exposed 3'-hydroxyl group recognized by an enzyme. The 3'-hydroxyl group can be easily utilized for the construction of a secondary product by an additional enzymatic process such as primer extension or ligation.

The invention claimed is:

1. A method for preparing a single-nucleotide (NT) incorporated DNA oligomer, comprising (a) preparing a DNA oligomer and a plurality of ribonucleotide triphosphates (rNTPs) and (b) allowing the DNA oligomer to react with the plurality of rNTPs in the presence of a TdT reaction buffer containing Tris-borate such that a ribose-borate complex is formed to inhibit the bonding between the plurality of rNTPs, leaving a single-incorporated rNTP at a 3'-end of the DNA oligomer.

2. The method according to claim 1, wherein the rNTP is selected from the group consisting of adenosine triphosphate (ATP), uridine triphosphate (UTP), guanosine triphosphate (GTP), oxanosine triphosphate (OTP), $N^6$-propargyl-ATP (N6P-ATP), aminoallyl-UTP (AA-UTP), biotin-16-UTP (Bt-UTP), and combinations thereof.

* * * * *

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence

```
<220> FEATURE:
<223> OTHER INFORMATION: DNA oligomer

<400> SEQUENCE: 1
aaaaaaaaaa                                                                10

<210> SEQ ID NO 2
<211> LENGTH: 19
<212> TYPE: DNA
<213> ORGANISM: Artificial Sequence
<220> FEATURE:
<223> OTHER INFORMATION: upstream fragment

<400> SEQUENCE: 2
ctcggtcgac agtctgcgg                                                      19

<210> SEQ ID NO 3
<211> LENGTH: 19
<212> TYPE: DNA
<213> ORGANISM: Artificial Sequence
<220> FEATURE:
<223> OTHER INFORMATION: downstream fragment

<400> SEQUENCE: 3
ccattcctga ttctaagtg                                                      19

<210> SEQ ID NO 4
<211> LENGTH: 40
<212> TYPE: DNA
<213> ORGANISM: Artificial Sequence
<220> FEATURE:
<223> OTHER INFORMATION: template fragment

<400> SEQUENCE: 4
cacttagaat caggaatgga ccgcagactg tcgacctgag                               40

<210> SEQ ID NO 5
<211> LENGTH: 40
<212> TYPE: DNA
<213> ORGANISM: Artificial Sequence
<220> FEATURE:
<223> OTHER INFORMATION: template fragment

<400> SEQUENCE: 5
cacttagaat caggaatggg ccgcagactg tcgacctgag                               40

<210> SEQ ID NO 6
<211> LENGTH: 40
<212> TYPE: DNA
<213> ORGANISM: Artificial Sequence
<220> FEATURE:
<223> OTHER INFORMATION: template fragment

<400> SEQUENCE: 6
cacttagaat caggaatggc ccgcagactg tcgacctgag                               40

<210> SEQ ID NO 7
<211> LENGTH: 40
<212> TYPE: DNA
<213> ORGANISM: Artificial Sequence
<220> FEATURE:
<223> OTHER INFORMATION: template fragment

<400> SEQUENCE: 7
cacttagaat caggaatggt ccgcagactg tcgacctgag                               40
```